(12) United States Patent
Heitmeier et al.

(10) Patent No.: US 8,571,491 B2
(45) Date of Patent: Oct. 29, 2013

(54) SYSTEMS AND METHODS FOR ENABLING WIRELESS FUNCTIONALITY IN ELECTRONIC DEVICES

(75) Inventors: Rolf Heitmeier, Baunatal (DE); Norbert Viehmann, Neuental (DE)

(73) Assignee: B. Braun Melsungen AG, Melsungen (DE)

( * ) Notice: Subject to any disclaimer, the term of this patent is extended or adjusted under 35 U.S.C. 154(b) by 178 days.

(21) Appl. No.: 13/357,091

(22) Filed: Jan. 24, 2012

(65) Prior Publication Data

US 2013/0189933 A1 Jul. 25, 2013

(51) Int. Cl.
*H04B 1/38* (2006.01)

(52) U.S. Cl.
USPC .................................... 455/90.1; 340/5.61

(58) Field of Classification Search
USPC ............. 455/90.1, 127.1; 320/108; 340/5.61
See application file for complete search history.

(56) References Cited

U.S. PATENT DOCUMENTS

| | | | |
|---|---|---|---|
| 5,596,567 A | 1/1997 | deMuro et al. | |
| 6,031,353 A | 2/2000 | Banyas et al. | |
| 6,605,922 B2 | 8/2003 | Tamai et al. | |
| 7,388,350 B1 | 6/2008 | Wright | |
| 7,489,102 B2 | 2/2009 | Purdy et al. | |
| 7,684,834 B2 | 3/2010 | Kangas et al. | |
| 7,701,171 B2 | 4/2010 | Defant et al. | |
| 7,710,285 B2 | 5/2010 | Miyajima et al. | |
| 7,715,884 B2 | 5/2010 | Book et al. | |
| 7,805,263 B2 | 9/2010 | Mack | |
| 7,808,205 B2 | 10/2010 | Rao et al. | |
| 7,834,583 B2 | 11/2010 | Elder et al. | |
| 2005/0102167 A1 | 5/2005 | Kapoor | |
| 2008/0309285 A1 | 12/2008 | Choksi et al. | |
| 2009/0160607 A1* | 6/2009 | Edwards et al. | 340/5.61 |
| 2009/0198372 A1 | 8/2009 | Hammerslag | |
| 2010/0156343 A1 | 6/2010 | Jung | |
| 2010/0161257 A1 | 6/2010 | Cornett et al. | |
| 2012/0169276 A1* | 7/2012 | Wang et al. | 320/108 |
| 2013/0043830 A1* | 2/2013 | Lin | 320/107 |
| 2013/0043836 A1* | 2/2013 | Hui | 320/108 |
| 2013/0133088 A1* | 5/2013 | Gunadisastra et al. | 726/34 |

FOREIGN PATENT DOCUMENTS

| | | | |
|---|---|---|---|
| EP | 1804393 A2 | 7/2007 | |
| WO | WO2004/038942 A1 | 5/2004 | |

OTHER PUBLICATIONS

International Search Report dated Apr. 2, 2013, application No. PCT/IB2012/002205.

* cited by examiner

*Primary Examiner* — Creighton Smith
(74) *Attorney, Agent, or Firm* — RatnerPrestia

(57) ABSTRACT

Modules, systems, and methods for enabling wireless functionality in electronic devices are disclosed. A module comprises a housing, a plurality of module terminals, a wireless transmitter, a first electronic component, and a power source. The housing is sized to be removably inserted in a power source receptacle of the electronic device. The plurality of module terminals contact a corresponding plurality of device terminals of the electronic device. The first electronic component is operable to receive outbound device data from the electronic device via the module terminal and transmit the outbound device data using the wireless transmitter. The power source is operable to provide power to the electronic device. The method comprises inserting a module in the power source receptacle of the electronic device, receiving outbound device data from the electronic device, and transmitting the outbound device data using the wireless transmitter.

18 Claims, 5 Drawing Sheets

SYSTEMS AND METHODS FOR ENABLING WIRELESS FUNCTIONALITY IN ELECTRONIC DEVICES

FIELD OF THE INVENTION

The present invention relates generally to wireless communication systems, and more particularly, to systems and methods for enabling wireless functionality in electronic devices.

BACKGROUND OF THE INVENTION

In recent years, the ability of electronic devices to communicate information to other electronic devices has grown in importance. In particular, electronic devices with wireless communication functionality have become particularly desirable, due in part to their ease of communication and portability. Electronic devices that lack wireless communication function have thus become disfavored, even when those devices' primary non-communication functions are still viable.

SUMMARY OF THE INVENTION

Aspects of the present invention relate to systems and methods for enabling wireless functionality in electronic devices.

In accordance with one aspect of the present invention, a module for enabling wireless functionality in an electronic device is disclosed. The module comprises a housing, a plurality of module terminals, a wireless transmitter, a first electronic component, and a power source. The housing is sized to be removably inserted in a power source receptacle of the electronic device. The plurality of module terminals is supported by the housing to contact a corresponding plurality of device terminals of the electronic device when the housing is received within the power source receptacle. The first electronic component is accommodated within the housing and associated with the wireless transmitter. The first electronic component is in communication with a first of the plurality of module terminals and is operable to receive outbound device data from the electronic device via the first module terminal and transmit the outbound device data using the wireless transmitter. The power source is accommodated within the housing. The power source is in communication with a second of the plurality of module terminals and is operable to provide power to the electronic device when the housing is received within the power source receptacle.

In accordance with another aspect of the present invention, a system for wirelessly communicating data is disclosed. The system comprises the above-described module, and the electronic device for receiving the module.

In accordance with yet another aspect of the present invention, a method for enabling wireless functionality in an electronic device is disclosed. The method comprises inserting a module in a power source receptacle of the electronic device such that a plurality of module terminals of the module contact a corresponding plurality of device terminals of the electronic device, providing power to the electronic device with a power source of the module via a second of the plurality of module terminals, receiving outbound device data from the electronic device with a first electronic component of the module via a first of the plurality of module terminals, and transmitting the outbound device data using a wireless transmitter of the module.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The modules, systems, and methods disclosed herein are usable in conjunction with electronic devices that lack wireless communications functionality and for selectively adding/removing wireless communications functions to/from electronic devices. These embodiments may be particularly suitable for providing wireless functionality to electronic devices that originally lack such features, i.e., to retrofit electronic devices with wireless functionality.

The exemplary electronic devices disclosed herein are described primarily with respect to infusion devices. However, while the exemplary embodiments of the present invention are described herein in the context of infusion devices, it will be understood by one of ordinary skill in the art that the invention is not so limited. The modules, systems, and methods described herein are usable to enable wireless functionality for any suitable electronic device.

The exemplary embodiments of the present invention generally relate to a battery pack module configured to retrofit an existing electronic device with wireless communication capability. The battery pack module is configured to receive signals from the electronic device through the standard battery terminals, and transmit the received signals wirelessly. The battery pack module is also configured to receive signals wirelessly, and transmit the received signals to the electronic device through the standard battery terminals.

Figure 1:
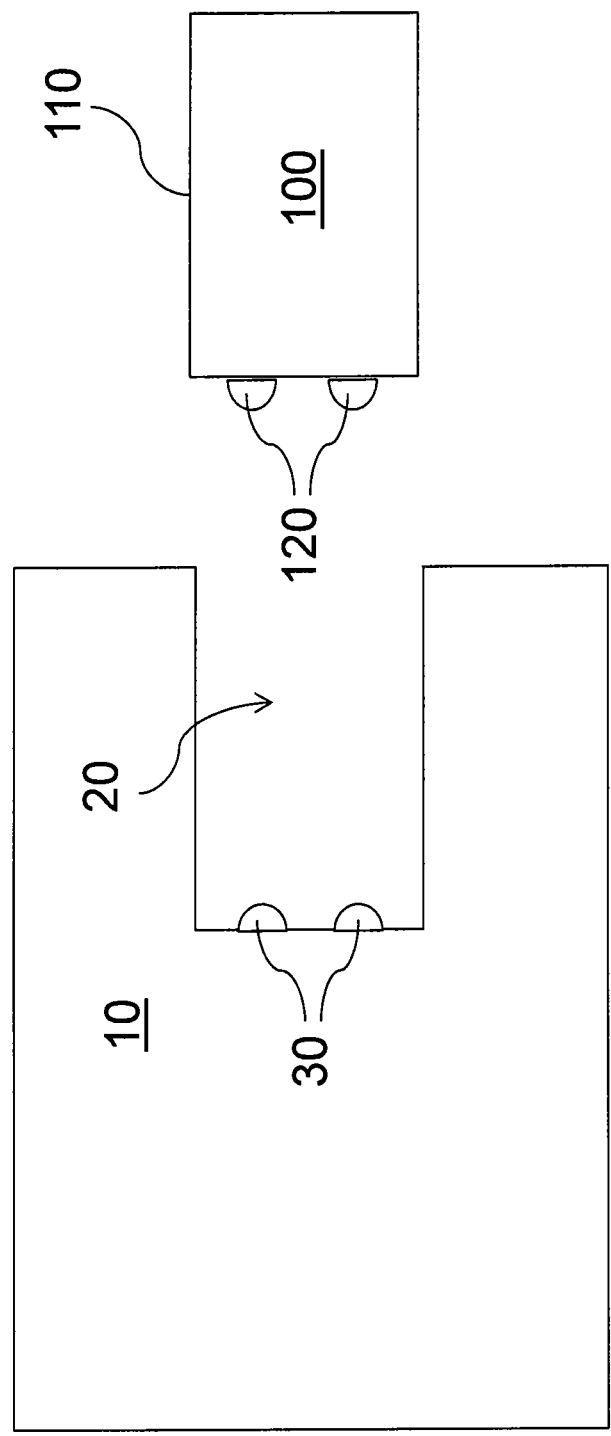
FIGS. 1 and 2 are diagrams illustrating an exemplary module for enabling wireless functionality in an electronic device in accordance with aspects of the present invention.
Figure 2:
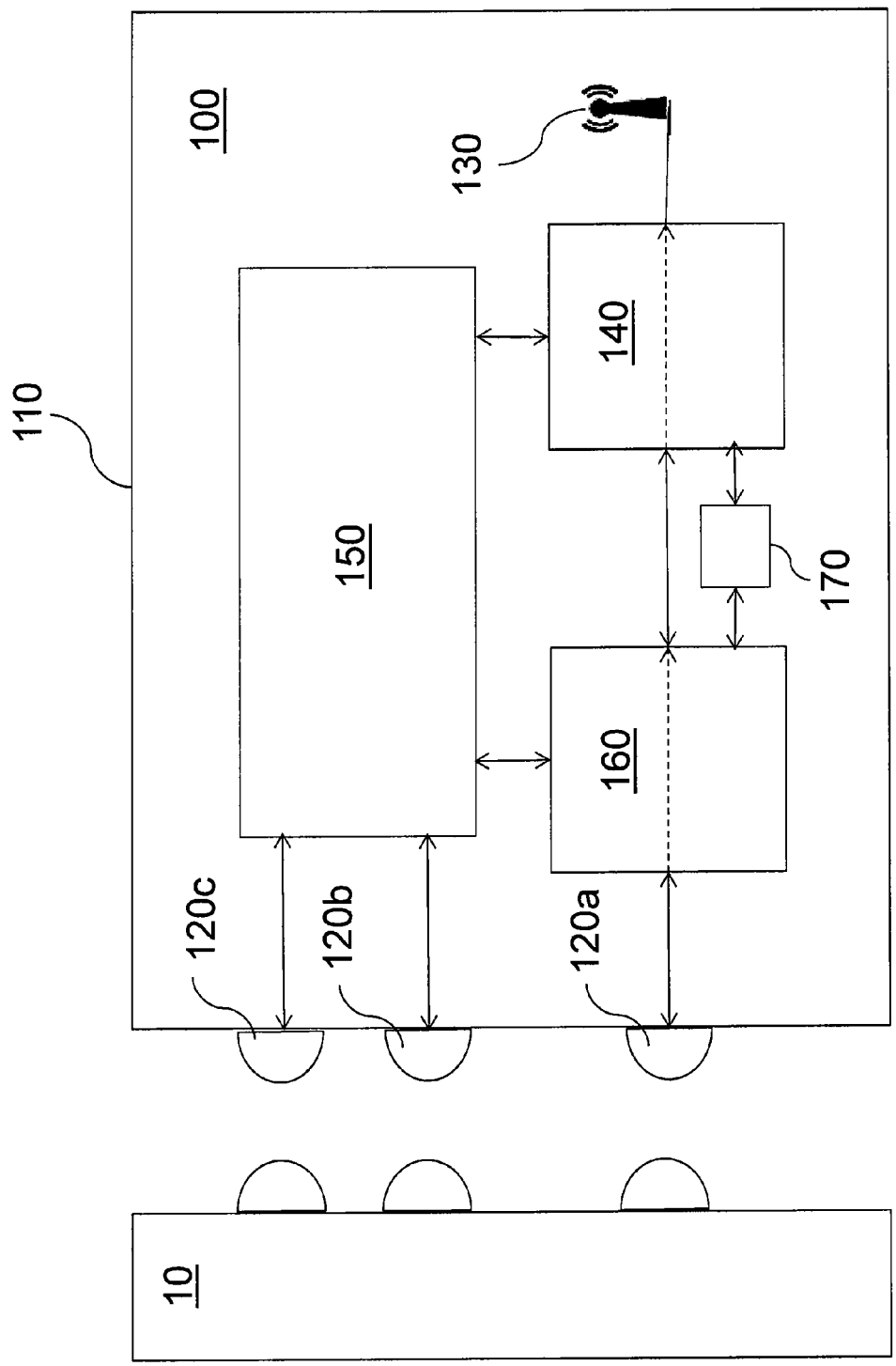

Referring now to the drawings, FIGS. 1 and 2 illustrate a module 100 for enabling wireless functionality in an electronic device in accordance with aspects of the present invention. Module 100 is usable to enable wireless communication functionality in an electronic device that originally lacks wireless functionality, e.g., electronic device 10. Electronic device 10 may be an electronic medical device such as, for example, an infusion device. As a general overview, module 100 includes a housing 110, a plurality of terminals 120, a wireless transmitter 130, an electronic component 140, and a power source 150. Additional details of module 100 are described herein.

Housing 110 houses the components of module 100. As shown in FIG. 1, electronic device 10 includes a power source receptacle 20. The power source receptacle 20 of electronic device 10 is sized to receive a power source such as a conventional battery pack. Housing 110 is sized to be removably inserted in power source receptacle 20, as shown in FIG. 1. Thus, housing 110 desirably has the size and shape of a conventional battery pack for electronic device 10. Suitable sizes and shapes for housing 110 may be readily determined by one of ordinary skill in the art based on the sizes and shapes of conventional battery packs for electronic device 10.

A plurality of module terminals 120 are supported by housing 110. Module terminals 120 may be directly or indirectly supported by housing 110. As shown in FIG. 1, electronic device 10 includes a plurality of device terminals 30 positioned in power source receptacle 20. Device terminals 30 are positioned to contact corresponding terminals on the conventional battery pack when the battery pack is received in power source receptacle 20, e.g., to receive power from the battery pack for powering electronic device 10. In one embodiment, module terminals 120 may be indented terminals, so as to prevent contact with metal surfaces, while device terminals 30 are projections sized to engage the indented module terminals. Device terminals 30 are conventionally used primarily for receiving power from a conventional battery pack. Module terminals 120 are positioned on housing 110 to contact device terminals 30 when module 100 is inserted in power source receptacle 20. Thus, positioning of module terminals 120 is desirably the same or similar to the terminals of the conventional battery pack for electronic device 10. While two module terminals 120 are illustrated in FIG. 1, it will be understood that the present invention is not so limited. Module 100 may include any number of module terminals 120, as would be understood by one of ordinary skill in the art from the description herein.

Wireless transmitter 130 is supported by housing 110. Wireless transmitter 130 may be accommodated within housing 110, or mounted on the surface of housing 130. Wireless transmitter is configured to transmit data wirelessly from module 100. Wireless transmitter 130 may further be a wireless transceiver, and be configured to receive data wirelessly. Wireless transmitter 130 is desirably usable to transmit data to and receive data from a remotely located electronic device within a wireless local area network (WLAN) of module 100. Additional details regarding transmissions made and received by wireless transmitter 130 will be provided herein. Suitable transmitters/receivers/transceivers for use as wireless transmitter 130 will be known to one of ordinary skill in the art from the description herein.

Electronic component 140 is associated with wireless transmitter 130. As shown in FIG. 2, electronic component 140 is in communication with one of the module terminals 120a. In an exemplary embodiment, electronic component 140 is a wireless computer adapted to control wireless transmissions made using wireless transmitter 130. In this embodiment, electronic component 140 is operable to receive outbound device data from electronic device 10 via module terminal 120a, and transmit the outbound device data to a remote location using wireless transmitter 130. Where wireless transmitter 130 is a wireless transceiver, electronic component 140 is further operable to receive inbound device data using the wireless transceiver, and transmit the inbound device data to electronic device 10 via module terminal 120a.

Electronic component 140 may also be configured to process data received from electronic device 10 or wireless transmitter 130 prior to or instead of transmitting the data. Electronic component 140 may comprise one or more data processors programmed to perform the above-described operations of electronic component 140. Electronic component 140 may further include a memory and software provided in the memory for operating the one or more processors. Suitable data processors will be known to one of ordinary skill in the art from the description herein.

While electronic component 140 is illustrated in FIG. 2 as being in communication with a single module terminal 120a, it will be understood that the present invention is not so limited. Electronic component 140 may be connected to any number of module terminals 120, as would be understood by one of ordinary skill in the art from the description herein.

Power source 150 is accommodated within housing 110. As shown in FIG. 2, power source 150 is in communication with other module terminals 120b and 120c. Power source 150 is operable to provide power to electronic device 10 (e.g., to enable operation of electronic device 10) via module terminals 120b and 120c when module 100 is received in power source receptacle 20. Power source 150 may further be configured to provide power to the components of module 100, e.g., electronic component 140. In an exemplary embodiment, power source 150 may be a rechargeable lithium-ion battery. The voltage, power, and lifetime of the battery may be selected to be compatible with the electronic device 10 to be charged by power source 150. Suitable batteries will be known to one of ordinary skill from the description herein.

It will be understood that module 100 is not limited to the above components, but may include alternative components and additional components, as would be understood by one of ordinary skill in the art from the description herein.

Module 100 may include another electronic component 160. Electronic component 160 is associated with power source 150. As shown in FIG. 2, electronic component 160 is in communication with module terminal 120a. In an exemplary embodiment, electronic component 160 is a battery controller adapted to control operation of power source 150. In this embodiment, electronic component 160 is operable to receive power source data from electronic device 10 via module terminal 120a, and control the operation of power source 150 based on the received power source data.

Electronic component 160 may also be configured to process data received from electronic device 10 prior to or instead of controlling the operation of power source 150. Electronic component 160 may comprise one or more data processors programmed to perform the above-described operations of electronic component 160. Suitable data processors will be known to one of ordinary skill in the art from the description herein.

Module 100 may also include a shutoff component 170. Shutoff component 170 may be programmed to disable wireless functionality upon receiving a signal from electronic component 140 or 160. In this embodiment, electronic device 10 may be programmed to send a signal to module 100 indicating that wireless functionality is unnecessary. Accordingly, shutoff component 170 may disable wireless transmitter 130 and electronic component 140, in order to enable module 100 to function similar to a conventional battery pack.

As illustrated in FIG. 2, both electronic component 140 and electronic component 160 may receive data from electronic device 10 via a single module terminal 120a. In this embodiment, electronic components 140 and 160 may be operable to receive the outbound device data and the power source data in serial communications from electronic device 10.

Figure 3:
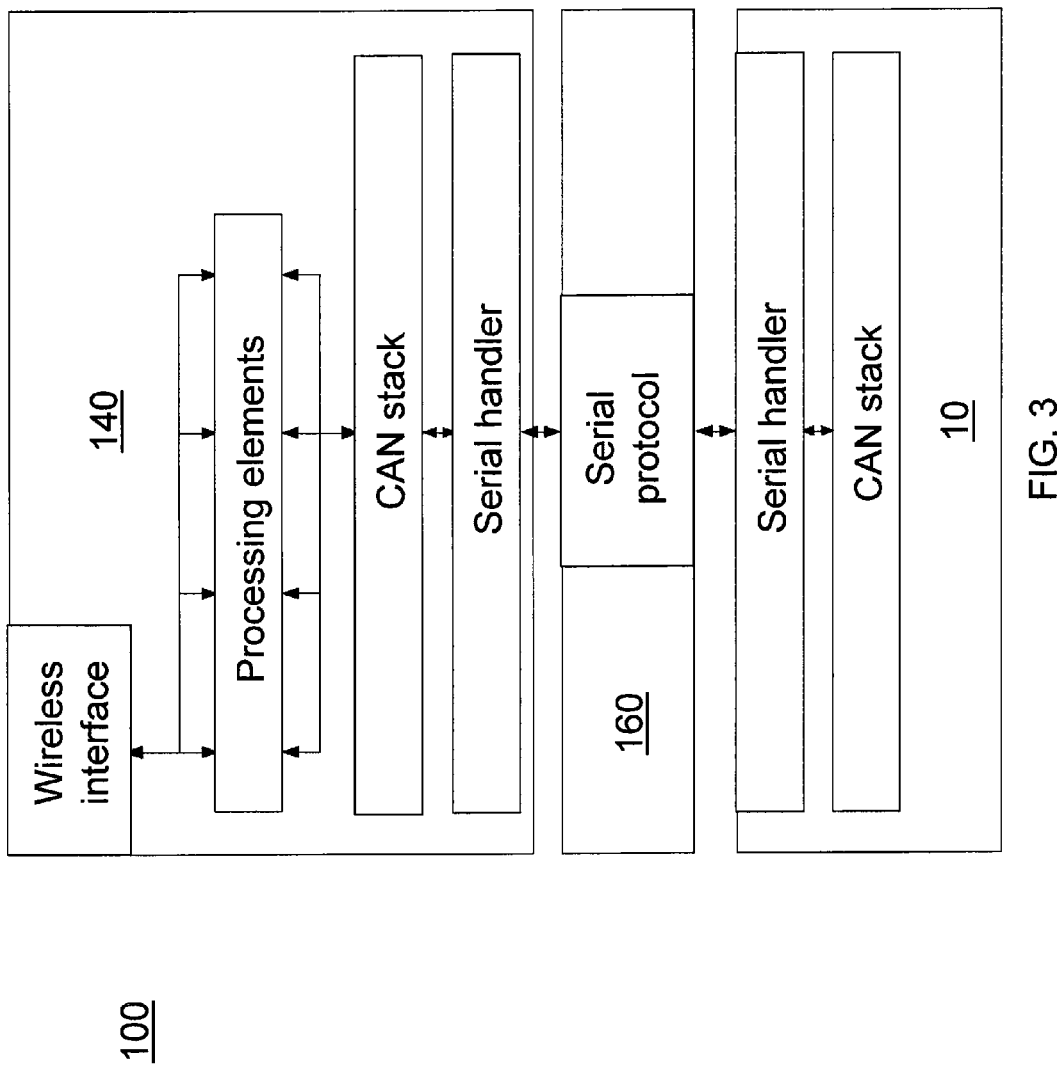
FIG. 3 is a flowchart illustrating an exemplary communication scheme for the module of FIG. 1.

FIG. 3 shows an exemplary communication scheme between electronic device 10 and electronic components 140 and 160 in accordance with aspects of the present invention. As shown in FIG. 3, electronic device 10 sends data to module 100 via serial communications through a single module terminal. In an exemplary embodiment, electronic component 160 is configured to first receive data from electronic device 10. Electronic component 160 is programmed to determine whether the received data is power source data meant for electronic component 160 (e.g., related to the operation or control of power source 150) or is outbound device data meant for electronic component 140 (e.g., device operating parameters for wireless transmission). In the former case, electronic component 160 processes the data received from electronic device 10, and determines whether any action must be taken. In the latter case, electronic component 160 is programmed to ignore the data, which is then serially communicated to electronic component 140.

Similarly, when electronic component 140 determines received data is power source data meant for electronic component 160, it is programmed to ignore that data. However, when electronic component 140 determines that it is the target of the received data, it is programmed to transmit or process the data.

Electronic components 140 and 160 use a serial protocol to analyze the data communicated through module terminal 120a to determine the intended target of the data. Suitable serial communications protocols will be known to one of ordinary skill in the art from the description herein.

While electronic components 140 and 160 are illustrated in FIGS. 2 and 3 as sharing a single module terminal 120a, it will be understood that the present invention is not so limited. Electronic components 140 and 160 may each be connected to their own module terminal(s) 120, depending on the construction of electronic device 10, as would be understood by one of ordinary skill in the art from the description herein.

Figure 4:
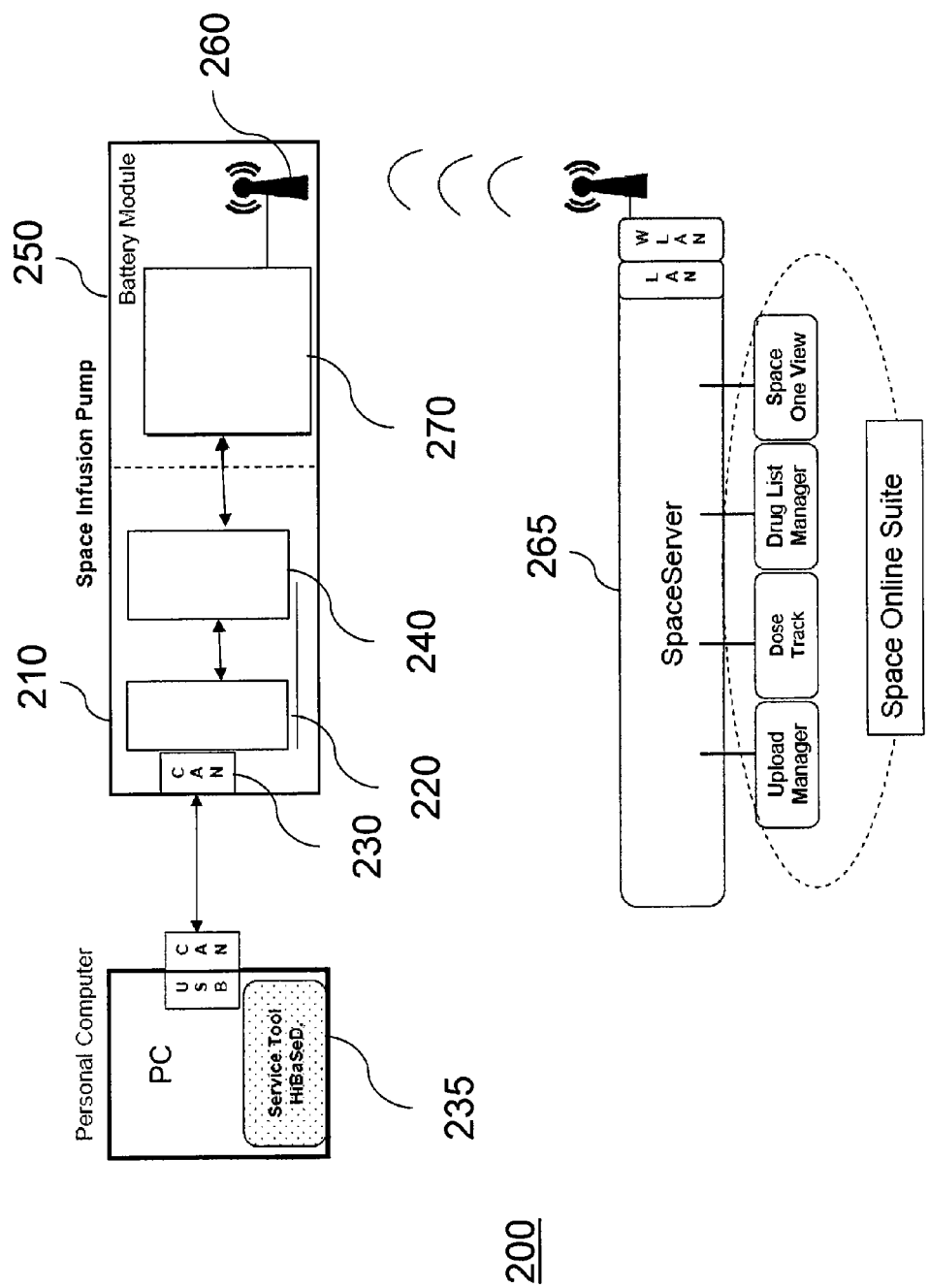
FIG. 4 is a diagram illustrating an exemplary system for wirelessly communicating data in accordance with aspects of the present invention.

FIG. 4 illustrates a system 200 for wirelessly communicating data in accordance with aspects of the present invention. As a general overview, system 200 includes an electronic device 210 and a module 250. Additional details of system 200 are described herein.

Electronic device 210 originally lacks wireless functionality. In other words, electronic device 210 is not constructed with the capability of sending or receiving wireless communications. Electronic device 210 may be capable of sending wired communications to another component. As set forth above with respect to electronic device 10, electronic device 210 includes a power source receptacle (not shown) including a plurality of device terminals (not shown) for receiving power from a conventional power source. In an exemplary embodiment, electronic device 210 is an electronic medical device such as, for example, an infusion device.

Electronic device 210 includes a functional component 220 that performs one or more functions of electronic device 10. Where electronic device 210 is an electronic medical device, functional component 220 may be configured to provide a medical treatment to a patient (e.g., infuse a fluid to a patient). Other suitable functional components 220 will be known to one of ordinary skill in the art from the description herein.

Electronic device 210 includes a controller area network (CAN) bus 230 for enabling transmission of wired communications to another device associated with electronic device 210. As shown in FIG. 4, system 200 may further include a computer 235 coupled to CAN bus 230 to receive data from electronic device 210.

Electronic device 210 includes a processor 240 that controls the operation of electronic device 210. Processor 240 operates functional component 220 to perform its corresponding function, e.g., providing treatment to a patient. Processor 240 further controls transmissions via CAN bus 230. Finally, processor 240 is configured to transmit data to module 250 when module 250 is received in the power source receptacle.

Electronic device 210 may include specialized software, or may be modified or updated to include specialized software, to enable electronic device 210 to communicate data for wireless transmission with module 250. In an exemplary embodiment, electronic device 210 may be programmed to determine (e.g., upon start-up) whether a conventional battery pack or module 250 is received in the power source receptacle. Where module 250 is received in power source receptacle, electronic device 210 may be programmed provide a user with options for communicating data with module 250 for wireless transmission. Through the use of software, wireless transmission may be retroactively added to an electronic device (e.g. electronic device 210) through only a software modification (i.e. the installation of the above specialized software), and without the need for an associated hardware modification.

Module 250 provides wireless functionality to electronic device 210. Module 250 includes all of the features set forth above with respect to module 100, except as otherwise provided.

Module 250 includes a wireless transceiver 260 and an electronic component 270 associated with the wireless transceiver. Wireless transceiver 260 is usable to transmit outbound device data to and receive inbound device data from a remotely located electronic device within a wireless local area network (WLAN) of module 250. As shown in FIG. 4, system 200 includes a remote server 265 operable to wirelessly receive data from and transmit data to wireless transceiver 260.

The operation of system 200 will now be described in accordance with aspects of the present invention. As set forth above, electronic device 210 lacks wireless functionality. When module 250 is inserted in power source receptacle of electronic device 210 (in place of a conventional battery pack), module 250 enables electronic device to perform wireless communications.

For example, processor 240 may transmit device data to module 250 via the battery terminals located in the power source receptacle. Electronic component 270 of module 250 is operable to receive the outbound device data from electronic device 210, and wirelessly transmit the outbound device data to server 265 using wireless transceiver 260. Similarly, module 250 may receive wireless transmissions from server 265 using wireless transceiver 260, and electronic component 270 may transmit the inbound device data from the wireless transmissions to electronic device 210 via the battery terminals.

Electronic device 210 may be programmed to transmit and receive different data via module 250 than it does via CAN bus 230. For example, when electronic device 210 is an infusion device, electronic device 210 may be operable to transmit data relating to configuration data (e.g., SSID, IP address, certificates, etc.) via CAN bus 230. Conversely, electronic device 210 may be operable to transmit data to module 250 representing infusion parameters for at least one patient of the infusion device. This infusion parameter data may then be wirelessly transmitted to server 265 by electronic component 270 for storage or generation of medical records. Similarly, electronic device 210 may be operable to receive data from server 265 representing an infusion parameter library for electronic device 210. The infusion parameter library data may then be transmitted to electronic device 210 for storage.

Figure 5:
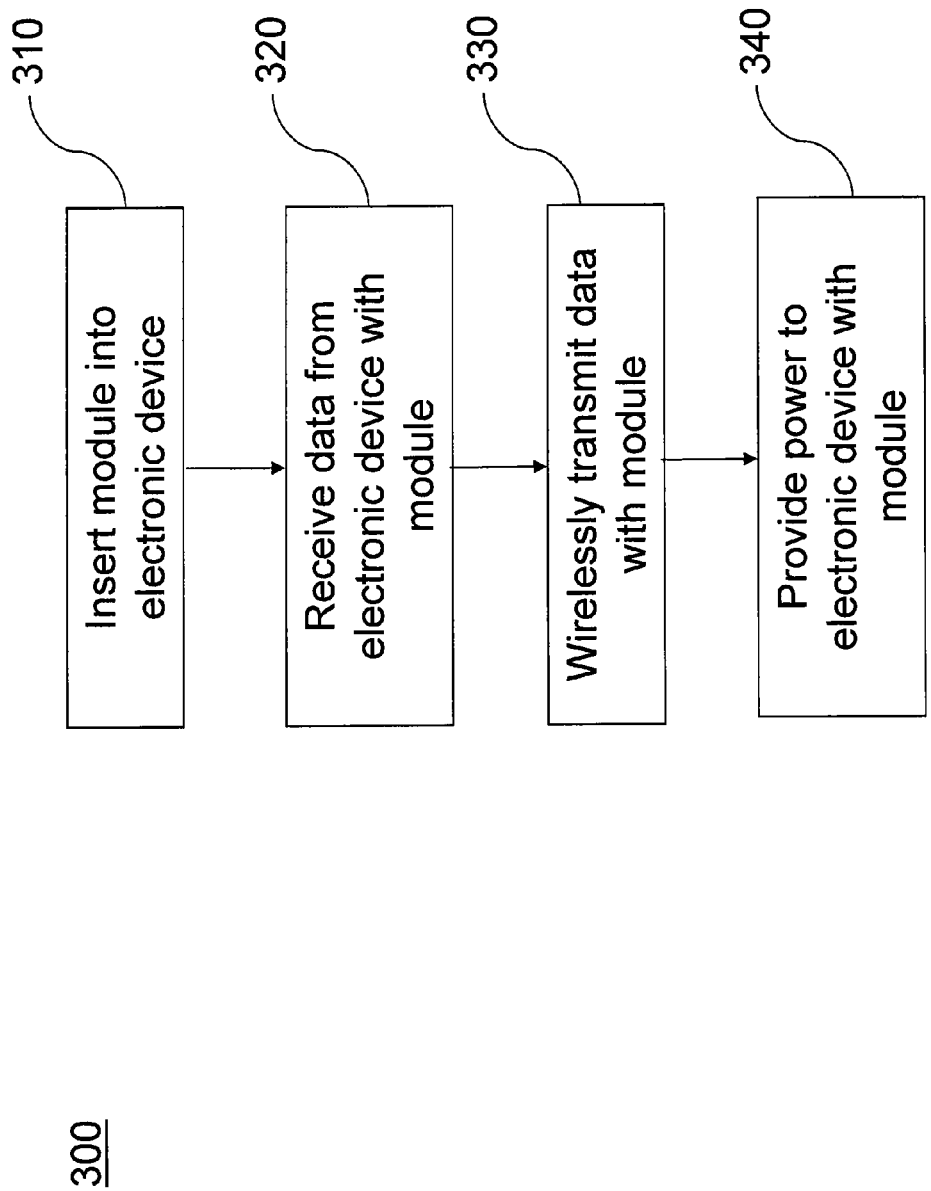
FIG. 5 is a flowchart illustrating an exemplary method for enabling wireless functionality in an electronic device in accordance with aspects of the present invention.

FIG. 5 shows an exemplary method 300 for enabling wireless functionality in an electronic device in accordance with aspects of the present invention. Method 300 is usable to enable wireless communication functionality in an electronic device that originally lacks wireless functionality. As a general overview, method 300 includes inserting a module into an electronic device, providing power to the electronic device, receiving data from the electronic device, and transmitting the data. Additional details of method 300 are described herein with respect to the components of electronic device 10 and module 100.

In step 310, a module is inserted into an electronic device. In an exemplary embodiment, module 100 is inserted into power source receptacle 20 of electronic device 10. Upon insertion, module terminals 120 of module 100 contact the corresponding device terminals 30 of electronic device 10.

In step 320, the module provides power to the electronic device. In an exemplary embodiment, power source 150 of module 100 provides power for operating electronic device 10 via module terminals 120b and 120c. Power source 150 may also provide power to the components of module 100 (e.g., electronic component 140).

In step 330, outbound device data is received from the electronic device. In an exemplary embodiment, electronic component 140 of module 100 receives outbound device data from electronic device 10 via module terminal 120a.

In step 340, the outbound device data is wirelessly transmitted. In an exemplary embodiment, electronic component 140 of module 100 transmits the outbound device data using wireless transmitter 130.

It will be understood that method 300 is not limited to the above steps, but may include alternative steps and additional steps, as would be understood by one of ordinary skill in the art from the description herein.

For one example, wireless transmitter 130 may be a wireless transceiver. Accordingly, method 300 may further include the steps of receiving inbound device data via the wireless transceiver, and transmitting the inbound device data to the electronic device. In an exemplary embodiment, electronic component 140 receives inbound device data using the wireless transceiver, and transmits the inbound device data to electronic device 10 via module terminal 120a. The wireless transmitter 130 may be operable to transmit data to and received data from a remotely located electronic device within a wireless local area network (WLAN) of module 100.

For another example, module 100 may include a second electronic component associated with the power source. Accordingly, method 300 may further include the steps of receiving power source data with the second electronic component, and controlling the power source based on the received power source data. In an exemplary embodiment, electronic component 160 receives power source data from electronic device 10 via module terminal 120a, and controls the operation of power source 150 based on the received power source data. Where both electronic component 140 and electronic component 160 receive data from electronic device 10 via the same module terminal 120a, they may be operable to receive the outbound device data and the power source data in serial communications from electronic device 10, substantially as described above.

For still another example, method 300 may include the step of removing a conventional battery pack from the electronic device. In an exemplary embodiment, a conventional battery pack is removed from power source receptacle 20 of electronic device 10 prior to step 310. Module 100 may then be inserted in power source receptacle 20 (i.e., in step 310), in order to switch a device from a non-wireless functionality mode to a wireless functionality mode. Likewise, module 100 may be replaced with a conventional battery pack to remove a wireless functionality mode, e.g., to free up module 100 for use in another device.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A module for enabling wireless functionality in an electronic device, the module comprising:
a housing sized to be removably inserted in a power source receptacle of the electronic device;
a plurality of module terminals supported by the housing to contact a corresponding plurality of device terminals of the electronic device when the housing is received within the power source receptacle;
a wireless transmitter supported by the housing;
a first electronic component accommodated within the housing and associated with the wireless transmitter, the first electronic component in communication with a first of the plurality of module terminals and operable to receive outbound device data from the electronic device via the first module terminal and transmit the outbound device data using the wireless transmitter; and
a power source accommodated within the housing, the power source in communication with a second of the plurality of module terminals and operable to provide power to the electronic device when the housing is received within the power source receptacle.

2. The module of claim 1, wherein the power source further provides power to the first electronic component.

3. The module of claim 1, wherein
the wireless transmitter comprises a wireless transceiver; and
the first electronic component is operable to receive inbound device data using the wireless transceiver and transmit the inbound device data to the electronic device via the first module terminal.

4. The module of claim 3, wherein the wireless transmitter is a wireless local area network transceiver.

5. The module of claim 1, further comprising:
a second electronic component associated with the power source, the second electronic component in communication with the first module terminal and operable to receive power source data from the electronic device via the first module terminal and control the operation of the power source based on the power source data.

6. The module of claim 5, wherein the first and second electronic components are operable to receive the device data and the power source data in serial communications from the electronic device via the first module terminal.

7. The module of claim 6, wherein the second electronic component is programmed to determine whether data received from the electronic device is the power source data or the outbound device data.

8. A system for wirelessly communicating data comprising:
the module of claim 1; and
the electronic device.

9. The system of claim 8, wherein the electronic device comprises an infusion device.

10. The system of claim 9, wherein
the outbound device data received by the first electronic component from the infusion device represents infusion parameters for at least one patient of the infusion device.

11. The system of claim 9, wherein
the first electronic component is operable to receive inbound device data using the wireless transceiver and transmit the inbound device data to the infusion device via the first module terminal, the received inbound device data representing an infusion parameter library for the infusion device.

12. A method for enabling wireless functionality in an electronic device, the method comprising:
    inserting a module in a power source receptacle of the electronic device such that a plurality of module terminals of the module contact a corresponding plurality of device terminals of the electronic device;
    providing power to the electronic device with a power source of the module via a second of the plurality of module terminals;
    receiving outbound device data from the electronic device with a first electronic component of the module via a first of the plurality of module terminals; and
    transmitting the outbound device data using a wireless transmitter of the module.

13. The method of claim 12, further comprising the step of providing power to the first electronic component with the power source.

14. The method of claim 12, further comprising the steps of receiving inbound device data using a wireless receiver of the module; and
    transmitting the inbound device data to the electronic device with the first electronic component via the first module terminal.

15. The method of claim 14, wherein the transmitting and receiving steps respectively comprise transmitting the outbound device data to and receiving the inbound device data from a remotely located device within a wireless local area network.

16. The method of claim 12, further comprising the steps of
    receiving power source data from the electronic device with a second electronic component of the module via the first module terminal; and
    controlling the operation of the power source with the second electronic component based on the power source data.

17. The method of claim 16, wherein the steps of receiving the outbound device data and the power source data with the first and second electronic devices, respectively, comprise receiving the data in serial communications from the electronic device via the first module terminal.

18. The method of claim 17, further comprising the step of:
    determining whether data received from the electronic device is the power source data or the outbound device data.

* * * * *